United States Patent [19]

Ninomiya et al.

[11] Patent Number: 5,481,109
[45] Date of Patent: Jan. 2, 1996

[54] SURFACE ANALYSIS METHOD AND APPARATUS FOR CARRYING OUT THE SAME

[75] Inventors: Ken Ninomiya, Higashi-Matsuyama; Hideo Todokoro; Tokuo Kure, both of Tokyo; Yasuhiro Mitsui, Fuchu; Katsuhiro Kuroda; Hiroyasu Shichi, both of Hachioji, all of Japan

[73] Assignee: Hitachi, Ltd., Tokyo, Japan

[21] Appl. No.: 211,575

[22] PCT Filed: Sep. 27, 1993

[86] PCT No.: PCT/JP93/01373

§ 371 Date: Apr. 11, 1994

§ 102(e) Date: Apr. 11, 1994

[87] PCT Pub. No.: WO94/08232

PCT Pub. Date: Apr. 14, 1994

[30] Foreign Application Priority Data

Sep. 28, 1992 [JP] Japan ................... 4-257789

[51] Int. Cl.⁶ .................. G01N 23/233; G01N 23/225; H01J 37/252
[52] U.S. Cl. .................. 250/310; 250/307; 250/397; 378/49
[58] Field of Search ................... 250/310, 307, 250/397; 378/49

[56] References Cited

FOREIGN PATENT DOCUMENTS 55-3129   1/1980   Japan ................... 250/310
61-132847  6/1987  Japan.
63-243855 10/1988  Japan.
5-52779    3/1993  Japan.
5-190633   7/1993  Japan.

*Primary Examiner*—Jack I. Berman
*Attorney, Agent, or Firm*—Fay, Sharpe, Beall, Fagan, Minnich & McKee

[57] ABSTRACT

A surface analysis method and an apparatus for carrying out the samein which the method involves the detection of fluorescence X-rays emitted from the surface of a sample in response to a finely focused electron beam irradiated thereto, whereby residues on the sample surface are analyzed qualitatively and quantitatively. An electron beam (1) is irradiated through a hole (9) at the center of an X-ray detector (8) into a fine hole (h) on the surface of a sample (2). In response, fluorescence X-rays are emitted from inside the fine hole (h) and are detected by an annular X-ray detector (8) having an energy analysis function near the axis of the electron beam (1) (preferably within 20 degrees with respect to the center axis of the electron beam). This arrangement allows the fluorescence X-rays from the fine hole (h) to reach the X-ray detector (8) without being absorbed by the substance of the material. That in turn ensures qualitative and quantitative analysis of high accuracy about residues in fine holes of large aspect ratios. Since the method is of non-destructive nature, the analyzed sample may be placed unscathed back into the fabrication process.

80 Claims, 8 Drawing Sheets

SURFACE ANALYSIS METHOD AND APPARATUS FOR CARRYING OUT THE SAME

TECHNICAL FIELD

The present invention relates to an improved surface analysis technique. More particularly, the invention relates to a surface analysis method for addressing the qualitative and quantitative analysis of residues remaining on the surface of samples to be analyzed, and to an apparatus for carrying out the same method.

BACKGROUND ART

To scale down the size of semiconductor devices requires establishing a viable fabrication technique for dealing with the levels of dimensions below deep submicrons. For example, the production of 256-Mb DRAM's necessitates fabricating contact holes as small as 0.2 μm in diameter and 2 μm in depth. To establish the fabrication technique of this magnitude of precision requires providing techniques for evaluating the precision of what is fabricated. Of such evaluation techniques, what is particularly in demand is one for analyzing qualitatively and quantitatively any residues that remain on the surface of wafers after dry etching. In analyzing such residues, it should be noted that the wafer surface is not necessarily flat; areas with large ups and downs symbolized by the contact holes above also need to be analyzed.

Heretofore, the analysis of residues over appreciably undulating areas has been generally carried out by cutting the fabricated wafer and by observing the cross section thereof using a scanning electron microscope (SEM). This method has a number of disadvantages. One disadvantage of the method is that it is simply for observing the shape of the residues and not for identifying them. Another disadvantage is that, the observed wafer cannot be returned whole into the fabrication process. A further disadvantage is that the conventional method is not fit for observing residues on the order of several nanometers. When the development of Gb-order semiconductor integrated circuit devices is concerned, the above-mentioned disadvantages are critical in that they can significantly degrade yield and analysis accuracy.

One conventional method that bypasses the need to cut the wafer for observation is the so-called fluorescence X-ray analysis. Japanese Patent Laid-Open No. 243855/1988 discloses an example of this method in the form of an analyzing apparatus using charged particles. The disclosed apparatus irradiates an electron beam to a sample and observes fluorescence X-rays emitted therefrom. The observation of fluorescence X-rays involves the use of crystals arranged at 22 degrees with respect to the center axis of the electron beam irradiated.

In analyzing residues qualitatively and quantitatively using fluorescence X-rays, what matters is where to locate means for observing the X-rays. That is, it is necessary to avoid the absorption of the fluorescence X-rays emitted from the sample by locating the observation means so that the position from which the X-rays emanate will be observed directly. However, there have been no definite criteria for locating the means for observing fluorescence X-rays, with little attention paid thereto. Illustratively, whereas the above-mentioned analyzing apparatus using charged particles has its crystals arranged at 22 degrees relative to the center axis of the generated electron beam, the angular arrangement is not fully capable of avoiding the absorption of the fluorescence X-rays emitted from the sample. In particular, the above analyzing apparatus is incapable of addressing DRAM's of 4 Mb or greater in capacity, the mainstay of semiconductor devices from now on, in analyzing qualitatively and quantitatively the surface residues of their samples.

DISCLOSURE OF INVENTION

It is therefore an object of the present invention to provide a surface analysis method for analyzing residues on the surface of a sample (such as a wafer) qualitatively and quantitatively with high accuracy without cutting it, and an apparatus for carrying out the same method.

In carrying out the invention, there is provided a surface analysis method for analyzing residues on the surface of a sample by irradiating an accelerated and focused electron beam onto the sample surface and by observing fluorescence X-rays emitted therefrom in return. The method characteristically involves observing the fluorescence X-rays near the center axis of the electron beam, the X-rays being emitted from the sample surface in response to the electron beam irradiated thereto.

According to one aspect of the invention, there is provided a surface analysis method for analyzing residues inside small holes on the surface of a sample by irradiating an accelerated and focused electron beam into the small holes and by observing fluorescence X-rays emitted therefrom in return, the surface analysis method comprising the step of observing the fluorescence X-rays within an angle α with respect to the center axis of the electron beam, the angle being defined as $$\tan \alpha = (a/d)$$

where, a multiplied by 2 stands for the inner diameter of any one of the small holes and d for the depth thereof.

According to another aspect of the invention, there is provided a surface analysis method for analyzing residues on the surface of a sample by irradiating an accelerated and focused electron beam onto the sample surface and by observing fluorescence X-rays emitted therefrom in return, the surface analysis method comprising the step of observing the fluorescence X-rays within an angle of 20 degrees with respect to the center axis of the electron beam.

The residues to be analyzed may include at least one atom selected from the group consisting of carbon atoms, oxygen atoms and silicon atoms. The energy of the electron beam is preferably such as to excite, for the purpose of fluorescence X-ray emission from the sample, at least one atom selected from the group consisting of carbon atoms, oxygen atoms and silicon atoms. Specifically, the energy of the electron beam is preferably not greater than 5 keV or not greater than 10 times the energy of the fluorescence X-rays to be observed.

The fluorescence X-rays may be observed by use of an annular X-ray detector which spectrally detects the fluorescence X-rays, the annular X-ray detector having a center hole coaxially arranged around the center axis of the electron beam. In this setup, the electron beam may be irradiated onto the sample surface through the center hole of the X-ray detector. The X-ray detector may be located inside an electron lens for focusing the electron beam.

The fluorescence X-rays may be observed by use of an X-ray detector located on the center axis of the electron beam, the X-ray detector detecting the fluorescence X-rays spectrally. In this case, the electron beam may be deflected to bypass said X-ray detector before being irradiated onto the sample surface.

The fluorescence X-rays may be observed by use of an X-ray reflector located near the center axis of the electron beam and by use of an X-ray detector located outside the center axis of the electron beam, the X-ray reflector reflecting the fluorescence X-rays, the reflected X-rays being spectrally detected by the X-ray detector. In this setup, the X-ray reflector may be a total reflector for totally reflecting the fluorescence X-rays. The X-ray reflector may also be a plane mirror. Alternatively, the X-ray reflector may be a cylindrical mirror, a spherical mirror, a toroidal mirror, or a non-spherical mirror comprising a revolutional conicoid. The curvature of the reflecting surface of the X-ray reflector may be varied as needed. Of course, if the fluorescence X-rays can be detected without setting the X-ray reflector, the X-ray detector located near and outside the center axis of the electron beam is only used for detecting the fluorescence X-rays.

The fluorescence X-rays may be observed by use of a multilayer film reflector located near the center axis of the electron beam and by use of an X-ray detector located outside the center axis of the electron beam, the multilayer film reflector spectrally reflecting the fluorescence X-rays, the spectrally reflected fluorescence X-rays being detected by the X-ray detector. Furthermore, the multilayer film reflector may be rotated to vary the spectral condition of the fluorescence X-rays, the X-ray detector being relocated in synchronism with the rotation of the multilayer film reflector so as to detect the spectrally reflected fluorescence X-rays.

The fluorescence X-rays may be observed by use of diffraction gratings located near the center axis of the electron beam and by use of an X-ray detector located outside the center axis of the electron beam, the diffraction gratings spectrally reflecting the fluorescence X-rays, the spectrally reflected fluorescence X-rays being detected by the X-ray detector.

The X-ray detector for detecting the fluorescence X-rays reflected spectrally by the multilayer film reflector or by the diffraction gratings may be a two-dimensional detector having a plurality of X-ray detecting devices arranged two-dimensionally.

The electron beam may be arranged to be deflected immediately before incidence on the sample surface.

Preferably, that spot on the sample surface to which the electron beam is irradiated is heated locally. The local heating is carried out preferably at a temperature between 100° C. and 200° C. The local heating may be carried out by focusing a light beam onto the spot to be heated. The light beam for the local heating may be either a visible ray beam or an infrared ray beam.

According to a further aspect of the invention, there is provided a surface analysis apparatus comprising electron beam irradiating means for irradiating a finely focused electron beam into small holes on the surface of a sample, and fluorescence X-ray observing means for observing fluorescence X-rays emitted from the small holes in response to the irradiation of the electron beam, wherein the fluorescence X-ray observing means includes a function for spectrally detecting the fluorescence X-rays emitted within an angle $\alpha$ with respect to the center axis of the electron beam, the angle being defined as $$\tan \alpha = (a/d)$$

where, a multiplied by 2 stands for the inner diameter of any one of the small holes and d for the depth thereof.

According to an even further aspect of the invention, there is provided a surface analysis apparatus comprising electron beam irradiating means for irradiating a finely focused electron beam onto the surface of a sample, and fluorescence X-ray observing means for observing fluorescence X-rays emitted from the sample surface in response to the irradiation of the electron beam, wherein the fluorescence X-ray observing means includes a function for spectrally detecting the fluorescence X-rays emitted within an angle of 20 degrees with respect to the center axis of the electron beam.

In a preferred structure according to the invention, the surface analysis apparatus may further comprise measuring means for measuring the location of the spot on the sample surface to which the electron beam is irradiated, and calculating means for calculating the distance between two different beam irradiated spot locations with reference to the location of the spot on the sample surface measured by the measuring means. This surface analysis apparatus may also comprise means for automatically determining the location to be analyzed on the sample surface in accordance with the data of the pattern coordinates established on the sample surface. The surface analysis apparatus may further comprise display means for displaying both the pattern coordinate data and an observed picture of a sample surface area including the location to be analyzed. The display means may have a function for displaying a schematic cross-sectional view of the sample surface area designated by the process data resulting from the surface processing carried out on the sample surface to be analyzed.

The operating principles of the invention outlined above will now be described. Irradiating an electron beam to a substance causes fluorescence X-rays to be emitted therefrom. The energy (wavelength) of the fluorescence X-rays is specific to the elements making up the substance. The invention takes advantage of this characteristic and is embodied to identify the elements, and the substance made thereof, by analyzing the energy of the fluorescence X-rays detected therefrom (i.e., qualitative analysis). Based on the emission intensity of the fluorescence X-rays detected, the invention makes it possible to acquire the quantity of the substance under observation (i.e., quantitative analysis).

Determining how to observe fluorescence X-rays is important in executing the analysis of residues over a considerably undulating surface of a wafer without breaking it. Principal residues from the process of semiconductor device fabrication include silicon oxide films and photoresist. To identify such residues requires detecting low Z elements such as C, O and Si. CK$\alpha$ X-rays and OK$\alpha$ X-rays generated by irradiation of an electron beam have low levels of energy (<1 keV). This means that these fluorescence X-rays cannot pass through an obstacle if any exists between their source and the means for observing them and thus cannot be detected. How such a situation can be brought about under the severest condition will be described below in more detail.

FIG. 2 shows an electron beam 1 being incident into a small hole h on the surface of a sample 2 to be analyzed. Fluorescence X-rays 5 are emitted from that spot of the hole bottom to which the electron beam is irradiated. As mentioned, the fluorescence X-rays 5 must be observed on condition that no obstacles exist between the source of the rays and the means for observing them. Referring to FIG. 2, the fluorescence X-rays 5 need to be observed from within a region A (referred to as "near the axis of the electron beam 1" hereunder). The angle $\alpha$ is defined as $$\tan \alpha = (a/d)$$

where, a multiplied by 2 stands for the inner diameter of the small hole and a for the depth thereof. An example of the small hole H is a contact hole of a DRAM. FIG. 3 depicts how the angle α changes along with the aspect ratio (2a/d) of the small hole h for DRAM's of varying integration densities. As evident from FIG. 3, DRAM's with integration densities of 4 Mb or greater, which are the mainstay of semiconductor devices from now on, need to be observed for the fluorescence X-rays within 20 degrees of angle α. Illustratively, the analyzing apparatus using charged particles disclosed in Japanese Patent Laid-Open No. 243855/1988 has crystals for fluorescence X-ray detection arranged at an angle of about 22 degrees with respect to the center axis of an incident electron beam. It follows that the disclosed apparatus is incapable of analyzing the inside of contact holes of DRAM's 4 Mb or greater in integration density. By contrast, the means for observing fluorescence X-rays according to the invention has part or all of the X-ray receiving surface of the X-ray detector located within the region A designated by the angle α in FIG. 2. Alternatively, the means of the invention for observing fluorescence X-rays has part or all of optical devices located within the same region A, the optical devices being furnished to guide fluorescence X-rays into the X-ray detector. The observing means of this kind may be embodied in diverse fashion, as will be described later. The use of such observing means permits qualitative and quantitative analysis of residues not only on the sample surface of negligible ups and downs but also on appreciably undulating surfaces of samples.

The acceleration energy of the electron beam will now be described. In an experiment, an electron beam was irradiated to silicon oxide films of varying thicknesses at acceleration energy levels of 2 keV and 5 keV. FIG. 4 shows how the resulting fluorescence X-rays (OKα X-rays having an energy level of about 0.5 keV) vary in intensity depending on the oxide film thickness. As shown in FIG. 4, the lower the acceleration energy of the electron beam, the higher the intensity of the fluorescence X-rays. The yield of fluorescence X-rays is a function of the acceleration energy of the electron beam irradiated. If the energy of fluorescence X-rays is represented by E, the yield thereof tends to be maximized when the acceleration energy of the irradiated electron beam is approximately equal to E multiplied by 3 (A. G. Michette; Optical Systems for Soft X-rays; Prenum Press, N.Y., 1986; p. 22). Further experiments revealed that CKα X-rays (having an energy level of about 0.3 keV) could be detected as an indication of the presence of residual photo-resist films on the order of nanometers when an electron beam was irradiated to the sample at energy levels of 1 to 2 keV. It was also revealed that the irradiation of an electron beam having an energy level of 2 through 5 keV was optimum for detecting the fluorescence X-rays emanating from silicon. From these experiments, it became clear that residues including such low Z elements as C, O and Si on the order of nanometers in thickness can be detected if the acceleration energy of the irradiated electron beam is limited to 5 keV or less.

The spatial resolution of fluorescence X-ray analysis will now be described. What primarily causes the spatial resolution to drop in analyzing fluorescence X-rays is the presence of reflected electrons. The effects of reflected electrons were examined in an experiment in which a pattern was formed using a silicon oxide film on a silicon wafer, with a 3-keV electron beam irradiated to a location at a distance x from the pattern side wall. When the reflected electrons caused fluorescence X-rays (OKα X-rays) to emanate from the pattern side wall, their intensity was measured. As illustrated in FIG. 5, irradiating the electron beam to a location 25 nm (distance x) away from the pattern side wall resulted in sufficiently low levels of the intensity of the fluorescence X-rays (OKα X-rays) emitted. It was found that the effects of the reflected electrons were negligible. Similar results were obtained when an electron beam 1.5 keV in acceleration energy was irradiated to resist patterns. More detailed experiments revealed that the effects of fluorescence X-rays caused by reflected electrons are virtually eliminated if the acceleration energy of the irradiated electron beam is not greater than 10 times the energy of the fluorescence X-rays to be detected. The spatial resolution as induced from FIG. 5 (on the order of nanometers) is sufficiently small compared with the minimum pattern size of DRAM's (about 1 μm for 4 Mb, 0.1 μm for 4 Gb). Thus the techniques proposed by the invention are favorable in analyzing the surface of semiconductor devices that are to be developed from now on.

As described, the invention involves irradiating an electron beam to the surface of a sample at an acceleration energy level of 5 keV or less and observing, near the axis of the electron beam, the fluorescence X-rays emitted from the sample surface. With the sample left unscathed during observation, any small residues over the sample surface on the order of nanometers are analyzed qualitatively and quantitatively with a spatial resolution of 0.1 μm or less.

The above and other objects, features and advantages of the present invention and the manner of realizing them will become more apparent, and the invention itself will best be understood from a study of the following description and appended claims with reference to the attached drawings showing some preferred embodiments of the invention.

BEST MODE FOR CARRYING OUT THE INVENTION

Preferred embodiments of the invention will now be described with reference to the accompanying drawings.

Figure 1:
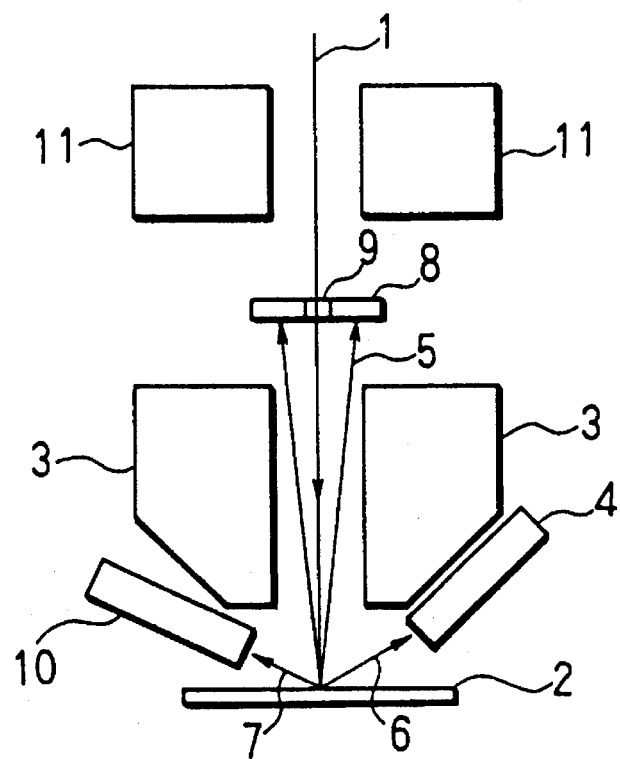
FIG. 1 is a schematic view of a surface analysis apparatus embodying the invention.

First Embodiment:

FIG. 1 schematically shows the most basic embodiment of the invention. Referring to FIG. 1, an accelerated electron beam 1 is irradiated perpendicularly to the surface of a sample 2 (e.g., semiconductor wafer) through a hole 9 at the center of an X-ray detector 8. The diameter of the electron beam 1 is sufficiently small compared with the area of the residues to be analyzed on the surface of the sample 2 (e.g., the area being equivalent to the diameter of a small hole thereon). The acceleration energy of the electron beam 1 is limited to 5 keV or less. The electron beam 1 is focused and accelerated by electron lenses 3 and 11. The hole 9 may be between 0.1 and 5 mm in diameter.

Figure 2:
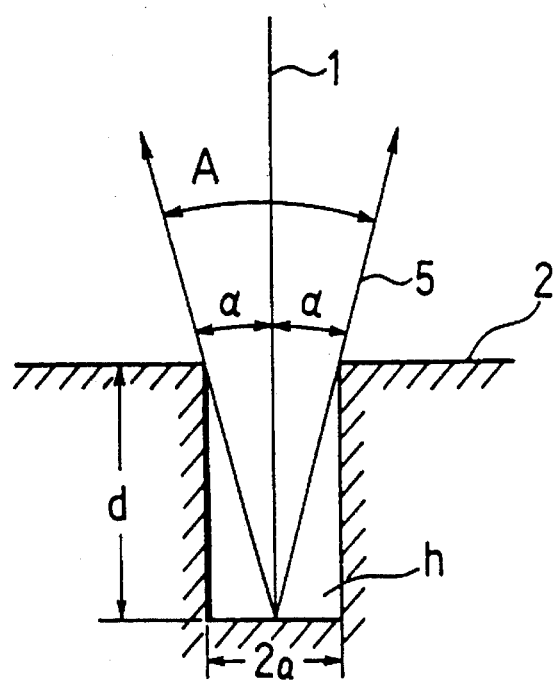
FIG. 2 is a schematic cross-sectional view showing where an X-ray detector is to be located in connection with the invention.
Figure 3:
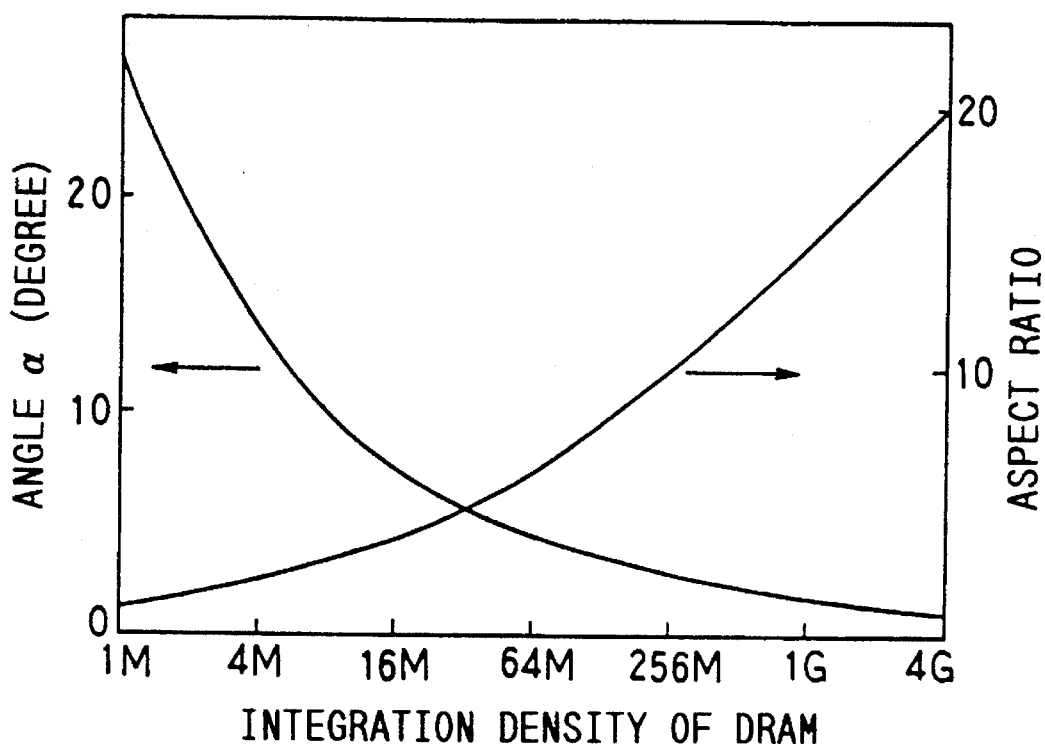
FIG. 3 is a graphic representation depicting how various parameters of DRAM's change in connection with the invention.
Figure 4:
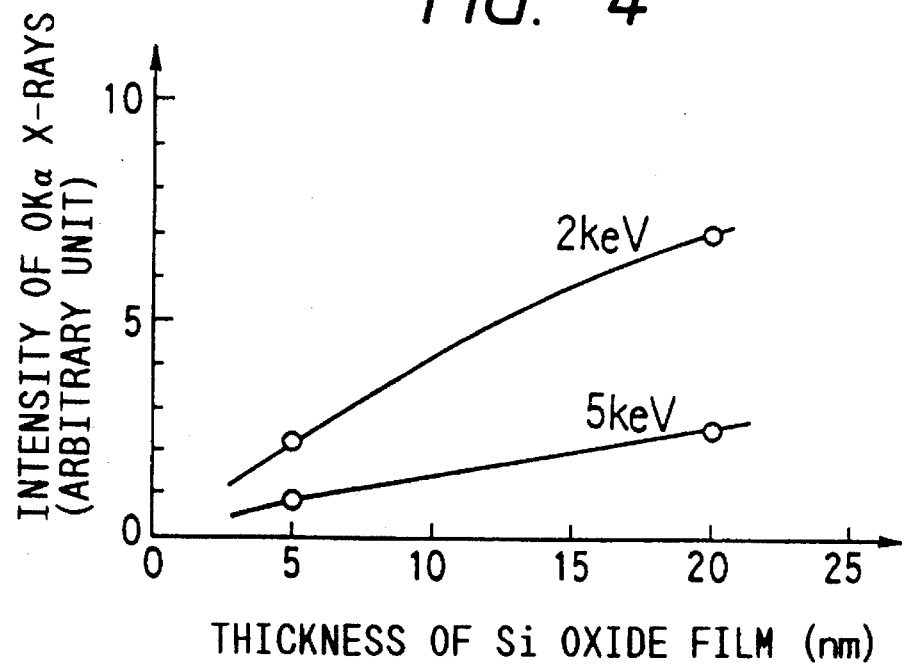
FIG. 4 is a graphic representation indicating typical dependence of the intensity of fluorescence X-rays on the thickness of silicon oxide films.
Figure 5:
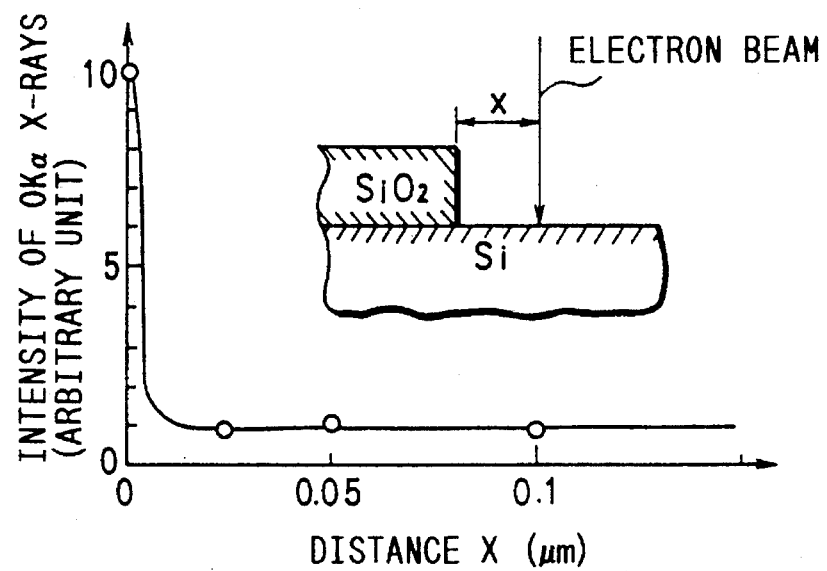
FIG. 5 is a graphic representation showing changes in the intensity of fluorescence X-rays emitted from the pattern side wall upon irradiation of reflected electrons to the wall.

Irradiating the electron beam 1 to the surface of the sample 2 causes fluorescence X-rays to emanate from the residues thereon. The emitted fluorescence X-rays are detected by an X-ray detector 8 furnished coaxially along the electron beam 1. The X-ray detector 8 is capable of analyzing energy and is typically implemented in the form of an X-ray solid state detector (SSD) or a harpicon (pickup tube). The detector 8 may be located anywhere in the axial direction of the electron beam 1; it may be located between the electron lenses 3 and 11 as shown in FIG. 1, or it may be located inside of the electron lens 3. What is important in setting up the X-ray detector 8 is that part or all of the X-ray receiving surface thereof must be positioned within the region A indicated in FIG. 2 (where the angle $\alpha$ is 20 degrees or less). It is under this condition that the X-ray detector 8 measures the fluorescence X-rays 5 for energy and intensity, whereby the residues on the sample surface are analyzed qualitatively and quantitatively.

Illustratively, fluorescence X-rays 6 having high energy levels such as SiK$\alpha$ X-rays can pass through a sample substance about several micrometers thick. Fluorescence X-rays of such high energy may be detected using an X-ray detector 4 located on one side of the position to which the electron beam is irradiated. This X-ray detector, too, can be one capable of analyzing energy such as an X-ray solid state detector. Comparing the signal output intensity of the X-ray detector 8 with that of the detector 4 makes it possible to know the attenuation rate of the fluorescence X-rays 6 having passed through the sample substance. The attenuation rate thus obtained is in turn used to acquire the transmission length of the fluorescence X-rays 6 through the sample substance. The transmission length thus known allows the observer illustratively to know the depths of small holes on the surface of the sample 2.

Irradiating the electron beam 1 to the surface of the sample 2 causes secondary electrons 7 to be emitted therefrom. A detector 10 is furnished to detect these secondary electrons 7. With the electron beam 1 scanning the surface of the sample 2, detecting the emitted secondary electrons 7 provides a secondary electron image of the sample surface. An observation of the secondary electron image makes it possible to grasp where the residues to be analyzed are located on the sample surface. That in turn makes it easy to determine the location to be analyzed on the sample surface.

With the first embodiment of the invention, the fluorescence X-rays 5 emitted from the surface of the sample 2 are observed near the axis of a low-energy electron beam 1 irradiated thereto. This makes it possible to analyze qualitatively and quantitatively any residues on a considerably undulating surface of the sample, accurately and without breaking the sample. Having undergone non-destructive analysis, the sample (e.g., semiconductor wafer) may be placed unscathed back to the fabrication process.

Figure 6:
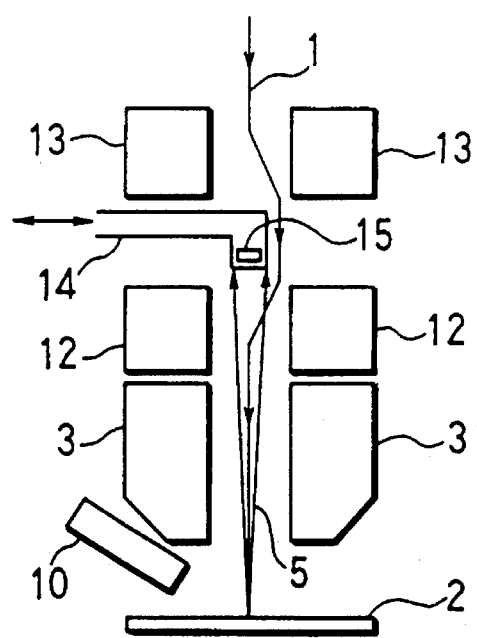
FIG. 6 is a schematic view of another surface analysis apparatus embodying the invention.

Second Embodiment:

FIG. 6 schematically depicts a second embodiment of the invention. This embodiment addresses the case where an X-ray detector 15 cannot have any hole (corresponding to the hole 9 in FIG. 1) made at the center thereof for letting the electron beam 1 pass through. The second embodiment utilizes an electron beam deflector 13 to deflect the electron beam 1 in one direction to let the beam bypass a housing 14 of the X-ray detector 15. Having passed by the housing 14, the electron beam 1 is deflected in the opposite direction by another electron beam deflector 12. As a result, the electron beam 1 returns to its original optical axis for perpendicular irradiation to the surface of the sample 2. The fluorescence X-rays 5 emitted from the sample surface upon irradiation of the electron beam 1 thereto are detected for energy analysis by the X-ray detector 15 located on the optical axis of the electron beam.

The housing 14 accommodating the X-ray detector 15 may be moved perpendicular to the optical axis of the electron beam 1. Where the position of the residue to be analyzed is to be determined illustratively by use of a secondary electron image, this setup allows the housing 14 to be retracted laterally from the optical axis. The electron beam 1 is arranged to scan the surface of the sample 2 for irradiation thereto while the deflectors 12 and 13 are not yet used to deflect the electron beam 1 (to bypass the X-ray detector). This makes it possible to observe the secondary electron image of the sample surface. After the location to be analyzed is identified by observation of the secondary electron image, the housing 14 is moved forward so that the detector 15 will be located on the optical axis. With the electron beam 1 deflected by the deflectors 12 and 13 (to bypass the X-ray detector), the electron beam 1 is irradiated to the target position on the surface of the sample 2. Because the electron beam 1 is not deflected while the position to be analyzed is being determined by observation of the secondary electron image, the target position may be determined with high resolution.

The second embodiment of the invention makes it possible to analyze residues on the sample surface particularly where a hole through which to pass the electron beam cannot be furnished at the center of the X-ray detector. The other effects of the second embodiment are the same as those of the first embodiment.

Figure 7:
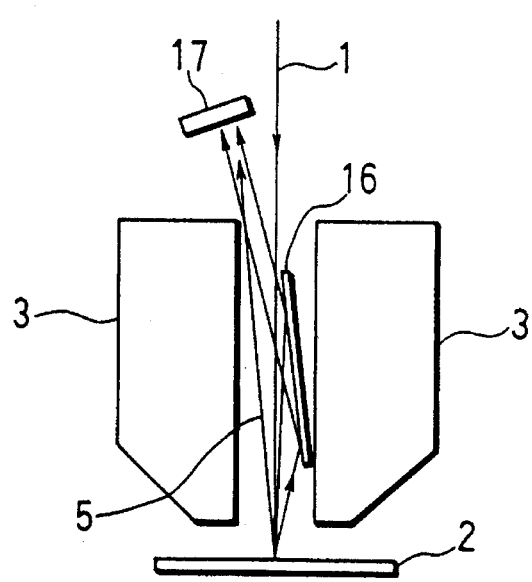
FIG. 7 is a schematic view of another surface analysis apparatus embodying the invention.

Third Embodiment:

FIG. 7 is a schematic view of a third embodiment of the invention. This embodiment utilizes an X-ray reflector 16 for guiding the fluorescence X-rays 5 from the surface of the sample 2 to an X-ray detector 17. Irradiating the electron beam 1 to the surface of the sample 2 causes fluorescence X-rays 5 to be emitted therefrom. The emitted fluorescence X-rays 5 from the sample surface are reflected by the X-ray reflector 16, reaching the X-ray detector 17 located off the optical axis of the electron beam. Although the X-ray reflector 16 may be made of any suitable material, the third embodiment has its reflector 16 equipped with a light reflecting surface composed of a gold or platinum layer deposited on a silicon wafer. (The deposited gold or platinum is effective in promoting the reflectance of X-rays.) Although FIG. 7 shows the X-ray reflector 16 as a plane mirror, a reflector with a curved surface may be used alternatively. Mirrors of the latter kind include a cylindrical mirror, a spherical mirror, and a non-spherical mirror such as a toroidal mirror or an ellipsoidal mirror. The X-ray reflector 16 may be located anywhere appropriate. The use of the X-ray reflector allows the fluorescence X-rays 5 within the region A of FIG. 2 to be guided efficiently towards the X-ray detector 17 positioned off the optical axis. The other features of the third embodiment are the same as those of the first or the second embodiment. The third embodiment offers the same effects as the first embodiment.

Figure 8:
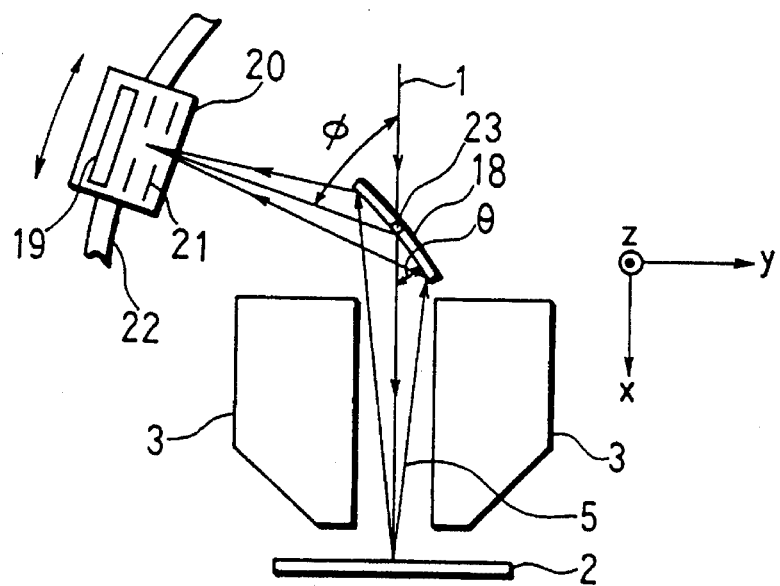
FIG. 8 is a schematic view of another surface analysis apparatus embodying the invention.

Fourth Embodiment:

FIG. 8 schematically depicts a fourth embodiment of the invention. As described, the first through the third embodiments use an X-ray detector capable of energy analysis for detecting fluorescence X-rays. Alternatively, the third embodiment (FIG. 7) may be arranged to have its reflector 16 furnished with a function of wavelength dispersion. That arrangement permits the use of an X-ray detector with no function for energy analysis. The fourth embodiment incorporates an arrangement of this kind.

Referring to FIG. 8, irradiating the electron beam 1 to the surface of the sample 2 causes fluorescence X-rays 5 to be emitted therefrom. The emitted fluorescence X-rays 5 are reflected by a reflector 18 before being detected by an X-ray detector 19. The reflector 18 comprises on its surface a multilayer reflecting film for X-ray reflection. The reflector 18 is located slightly off the center axis of the electron beam (0.1 to 2 mm away) so as not to obstruct the irradiation of the electron beam 1 to the sample surface. Alternatively, a plurality of reflectors may be arranged to encompass the center axis of the electron beam 1. The reflector 18 is furnished rotatably on a center axis 23 in parallel with the Z axis. The rotation, not shown, of the reflector 18 is carried out by a rotating mechanism using a pulse motor or the like.

The multilayer film reflector is a reflector constituted by a plurality of thin films of two different substances (e.g., Mo and Si) deposited alternately and cyclically on a substrate. If D stands for the thickness of one cycle of the deposited component films and θ for the incident angle of X-rays on the reflector, only the X-rays having the wavelength A that satisfies the relation $$2D \sin\theta = \lambda$$

are reflected by the X-ray reflector. Thus if the incident angle θ of X-rays is varied using a multilayer film reflector whose length of one cycle D is known, it is possible to analyze spectrally the X-rays that are incident on the reflector (i.e., energy analysis). The length of one cycle D for the multilayer film reflector is set preferably to 1 through 20 nm The fourth embodiment of FIG. 8 operates on the principle of spectrometry outlined above. That is, the reflector 18 is rotated around the center axis 23 so as to vary the incident angle θ of fluorescence X-rays 5 on the reflector 18. The X-ray detector 19 is moved in keeping with the rotation of the reflector 18 in order to detect the fluorescence X-rays 5 reflected spectrally by the reflector 18. The movement of the detector 19 is accomplished by relocating along a guide 22 a stage 20 that carries the detector 19. The relocation of the stage 20 is controlled by a relocating mechanism, not shown, which illustratively activates a pulse motor in synchronism with the rotation of the reflector 18 on condition that $$\phi = 2\theta$$

where φ represents the angle formed between the center position of the detector 19 as viewed from the center axis 23 of the reflector 18 on the one hand, and the center axis of the electron beam 1 on the other. A collimator 21 is provided to prevent unnecessary X-rays from reaching the X-ray detector 19.

The reflector 18 shown in FIG. 8 has a slightly curved surface with the ability of focusing. However, it is not mandatory to furnish the reflector with the focusing capability. What is essential with the fourth embodiment is the use of a multilayer film reflector for spectrally reflecting fluorescence X-rays. The reflector 18 may be shaped and located as desired and as needed. The fourth embodiment also provides the same effects as the first embodiment.

Figure 9:
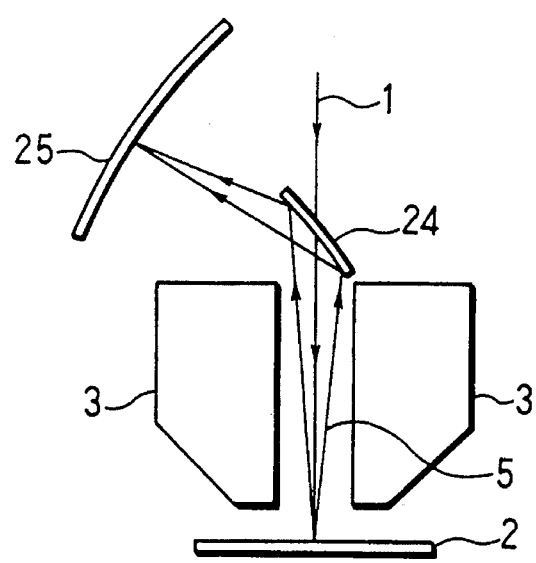
FIG. 9 is a schematic view of another surface analysis apparatus embodying the invention.

Fifth Embodiment:

FIG. 9 schematically depicts a fifth embodiment of the invention. This embodiment is another example of using an X-ray detector that has no function for energy analysis.

In place of the multilayer film reflector, the fifth embodiment utilizes diffraction gratings 24 as an optical device for spectral processing. The fluorescence X-rays 5 emitted from the surface of the sample 2 enter the diffraction gratings 24 located near the axis of the electron beam 1 for spectral diffraction. The diffracted fluorescence X-rays are detected by a defector 25. The detector 25 is a two-dimensional detecting device array comprising a large number of detecting devices arranged in two-dimensional fashion. Constituted in this way, the detector 25 permits spectral observation of multiple wavelengths on a concurrent basis. This means that the fifth embodiment takes appreciably less time than the fourth embodiment in executing the analysis. The other aspects of the fifth embodiment are the same as those of the fourth embodiment.

Figure 10:
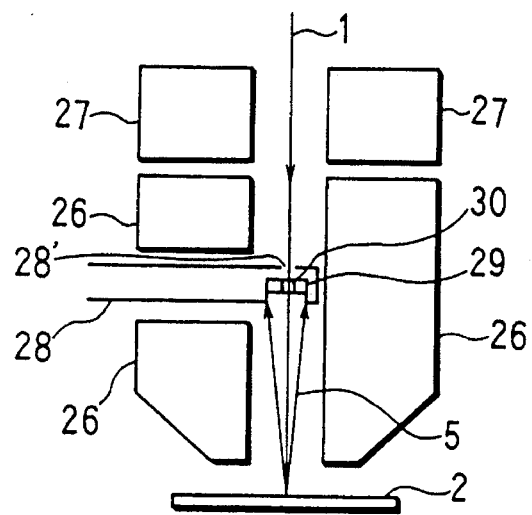
FIG. 10 is a schematic view of another surface analysis apparatus embodying the invention.

Sixth Embodiment:

FIG. 10 is a schematic view of a sixth embodiment of the invention. This embodiment has a coaxial type X-ray detector 29 located inside an electron lens 26, the detector being capable of analyzing energy. The electron beam 1 that enters the electron lens 26 through an electron lens 27 passes through two holes: a small hole 28' made on the housing 28 that holds the X-ray detector 29, and a center hole 30 of the detector 29. Past these holes, the electron beam 1 is irradiated perpendicularly to the surface of the sample 2. The fluorescence X-rays 5 emitted from the sample surface are detected by the X-ray detector 29.

Although the sixth embodiment uses the coaxial type detector 29 to detect the fluorescence X-rays 5, the reflector 18 (FIG. 8) or diffraction gratings 24 (FIG. 9) may also be installed inside the electron lens 26. In the latter case, it is obviously necessary to secure a sufficient space inside the electron lens 26 through which to let the reflected or diffracted fluorescence X-rays 5 pass in such a manner that the X-rays 5 will reach the detector 19 or 25.

Because the sixth embodiment allows the detector 29 to be set up closer to the sample 2, a higher level of signal intensity is obtained. That in turn boosts the sensitivity of analysis and enables residues of smaller dimensions to be analyzed.

Figure 11:
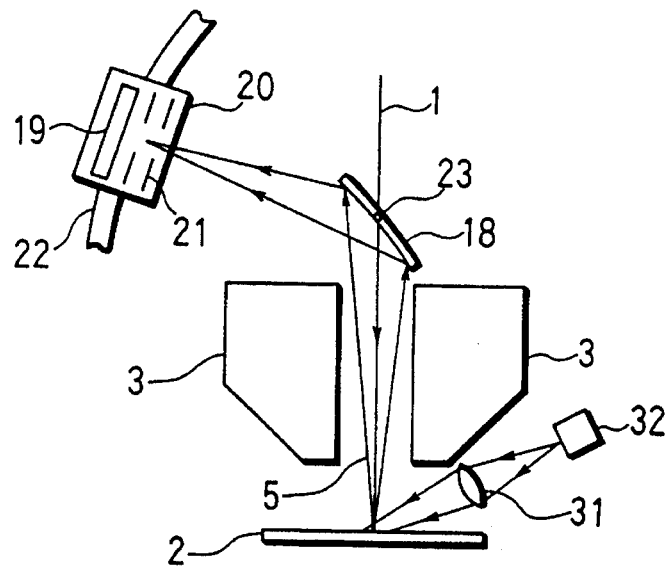
FIG. 11 is a schematic view of another surface analysis apparatus embodying the invention.

Seventh Embodiment:

FIG. 11 schematically shows a seventh embodiment of the invention. To analyze the residue inside a small hole on the sample surface requires irradiating the electron beam in the form of a point beam into the hole having a diameter on the submicron order. If the degree of vacuum is insufficient inside a vacuum chamber where the sample is placed (i.e., sample chamber), point-beam irradiation of the electron beam can contaminate the irradiated area with carbon atoms or the like. The seventh embodiment is designed specifically to prevent this kind of contamination from occurring.

The seventh embodiment includes heating means for heating the surface of the sample 2 to prevent the above contamination. More specifically, a focusing lens 31 is used to focus light (e.g., visible or infrared rays) from a light source 32 for irradiation onto the sample surface. The surface of the sample 2 may be heated to a temperature between 100° and 200° C. There is no need to heat the entire surface of the sample 2; a limited area between tens of μm and 1 mm in diameter need only be heated locally, the area including the spot to which the electron beam 1 is irradiated. The heating of this kind is readily accomplished by getting a suitable lens to focus the light of a commercially available light source onto the sample surface for several to tens of seconds.

Although the seventh embodiment utilizes the lens 31 to focus the light for heating, other optical devices for heating purposes may be used instead. For example, the use of a total reflector permits focusing without chromatic aberration, which is convenient for heating a very small area. Needless to say, the heating means of the seventh embodiment for heating the surface of the sample 2 may also be added to any other embodiment of the invention.

Because the seventh embodiment of the invention heats that spot on the sample surface to which the electron beam is irradiated, it is possible to analyze residues with high accuracy thanks to the reduced effects of contamination. The seventh embodiment is particularly suited for high-precision analysis of residues that contain carbon atoms such as resist.

Figure 12:
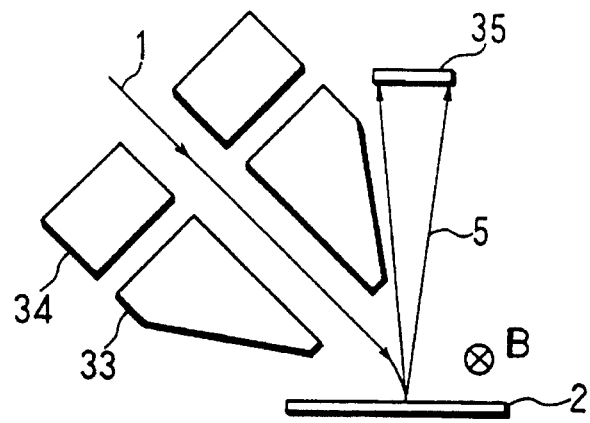
FIG. 12 is a schematic view of another surface analysis apparatus embodying the invention.

Eighth Embodiment:

FIG. 12 schematically depicts an eighth embodiment of the invention. For the embodiments described so far, the locus of the electron beam 1 is substantially linear with the exception of the second embodiment. Meanwhile, there are cases where the setting of an X-ray detector is made simpler by gently bending the locus of the electron beam 1 before it reaches the surface of the sample 2. The eighth embodiment is designed to provide this feature.

The eighth embodiment causes the electron beam 1 gently to deflect immediately before incidence onto the surface of the sample 2 past electron lenses 34 and 33. The deflection is achieved illustratively by forming a magnetic field B perpendicular to the view of FIG. 12 as the reader looks at it. (Means for forming the magnetic field is omitted from the figure to clarify the essence of the eighth embodiment.) It is assumed that the deflected electron beam 1 is incident on the surface of the sample 2 in a substantially perpendicular manner. The fluorescence X-rays 5 emitted from the sample surface upon irradiation of the electron beam 1 thereto are detected by a detector 35 capable of energy analysis. The multilayer film reflector 18 of the fourth embodiment or the diffraction gratings 24 of the fifth embodiment may also be used as spectral processing means for the fluorescence X-rays 5.

Although the eighth embodiment utilizes the magnetic field B to deflect the electron beam 1, other deflecting means may also be adopted. What is essential with the eighth embodiment is that deflecting the electron beam 1 immediately before incidence on the surface of the sample 2 allows the detector 35 to be set up easily. That in turn makes it easy to detect the fluorescence X-rays 5 emitted near the axis of the electron beam 1 that is incident on the sample surface.

According to the eighth embodiment, the electron beam 1 is deflected before incidence on the surface of the sample 2 so that a wide space will be secured in which the detector 35 is set up more easily than before. With more diverse kinds of X-ray detector to choose from for use with the embodiment offering the above feature, the constitution of the embodiment is simplified.

Figure 13:
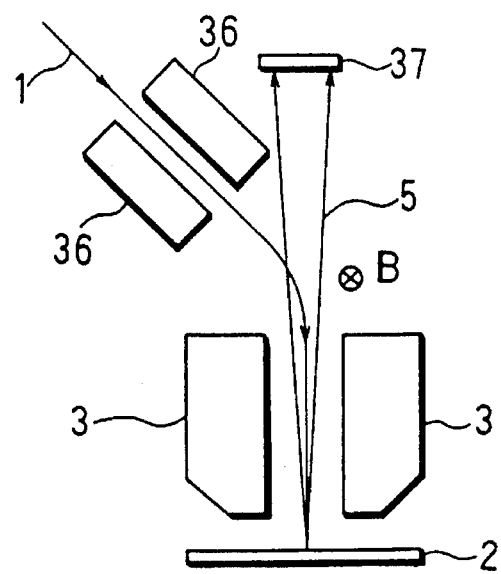
FIG. 13 is a schematic view of another surface analysis apparatus embodying the invention.

Ninth Embodiment:

FIG. 13 is a schematic view of a ninth embodiment of the invention. Whereas the eighth embodiment has the electron beam 1 deflected immediately before the surface of the sample 2, the electron beam 1 may also be deflected elsewhere. The ninth embodiment is an example in which the electron beam 1 is deflected away from the sample surface.

Referring to FIG. 13, the electron beam 1 is deflected between electron lenses 36 and 3. After deflection, the electron beam 1 is made perpendicularly incident on the surface of the sample 2. The fluorescence X-rays 5 emitted from the surface of the sample 2 (i.e., the fluorescence X-rays emitted near the axis of the deflected electron beam) are detected by a detector 37 located directly above the sample 2. As with the eighth embodiment, the electron beam 1 is deflected by use of the magnetic field B. The other aspects of the ninth embodiment are the same as those of the eighth embodiment. The ninth embodiment offers the same effects as the eighth embodiment.

Figure 14:
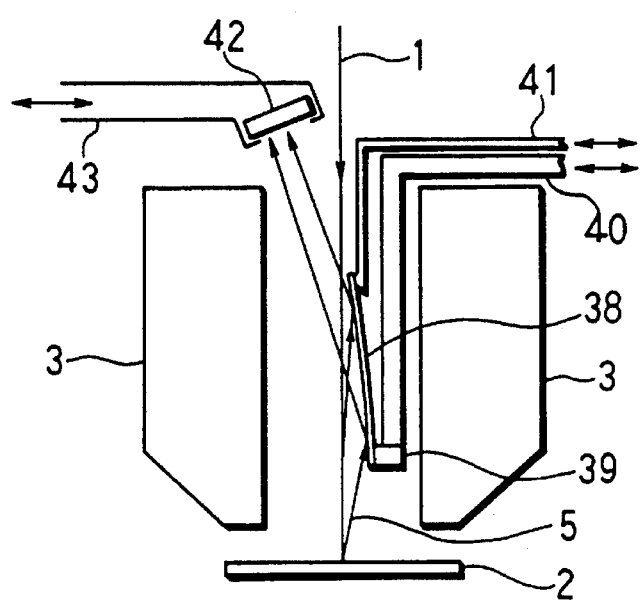
FIG. 14 is a schematic view of another surface analysis apparatus embodying the invention.

Tenth Embodiment:

FIG. 14 schematically shows a tenth embodiment of the invention. If the third embodiment (FIG. 7) has the curvature of the reflector 16 made variable, it is possible to focus more efficiently the fluorescence X-rays 5 emitted from the surface of the sample 2. The tenth embodiment is one example in which the curvature of the reflector is thus made variable to achieve that effect.

Referring to FIG. 14, the material of a reflector 38 is the same as that of the reflector 16 in the third embodiment. The difference is that the reflector 38 is physically flexible in its entirety. One end of the reflector 38 is fixed to a support base 39 which in turn is attached to a movable arm 40. The arm 40 may be moved in the arrowed direction. The other end of the reflector 38 is left free; the back of that end may be pushed by a fine-adjustment arm 41 whose movement may be fine-adjusted in the arrowed direction. The curvature of the reflector 38 is set as desired by operating the fine-adjustment arm 41 for adjusting the free-end position of the reflector 38. When the curvature of the reflector 38 is changed, the reflecting direction and focusing condition of the fluorescence X-rays 5 are also changed. This requires adjusting accordingly the location of a detector 42 capable of energy analysis. The location of the detector 42 is adjusted by moving in the arrowed direction a housing 43 containing the detector 42. The remaining constitutional aspects of the tenth embodiment are the same as those of the third embodiment.

Because the tenth embodiment allows the curvature of the reflector 38 to be varied, it is possible to focus the fluorescence X-rays 5 efficiently for incidence onto the detector 42. As a result, the sensitivity of residual analysis is improved.

Figure 15:
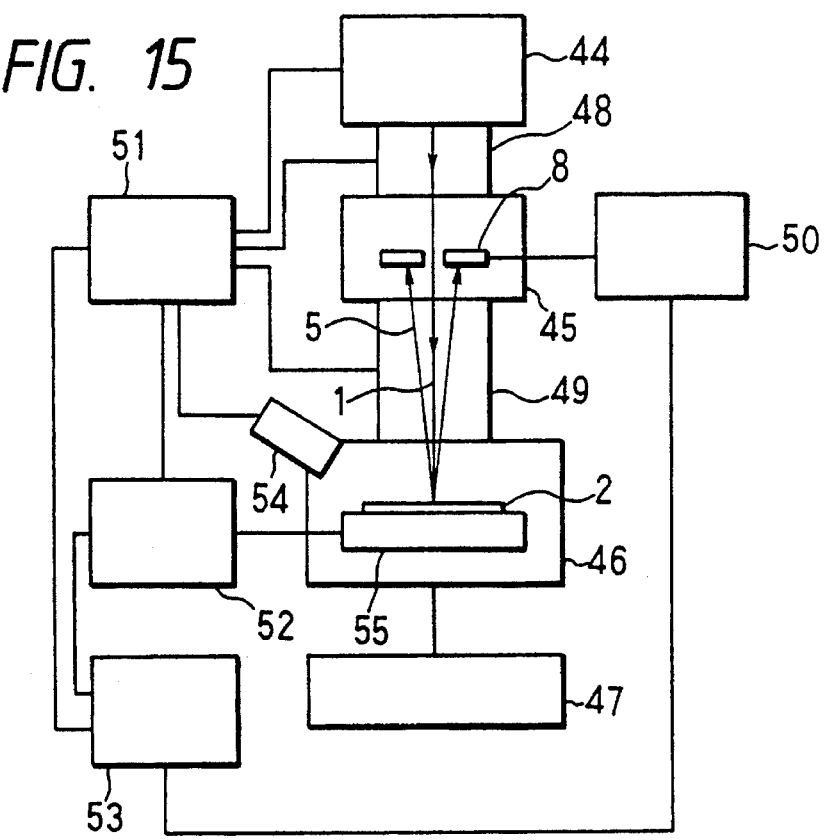
FIG. 15 is a schematic view of another surface analysis apparatus embodying the invention.

Eleventh Embodiment:

FIG. 15 is a schematic view of an eleventh embodiment of the invention. Any one of the first through the tenth embodiments discussed above may be equipped with additional functions to expand its versatility. The additional functions include a function to measure lengths of fine patterns and a function to further accelerate the electron beam. The eleventh embodiment is one example in which these functions are implemented.

Referring to FIG. 15, the electron beam 1 from an electron source 44 is accelerated and focused by electron lens systems 48 and 49 for irradiation to the surface of the sample 2 placed within a sample chamber 46. Needless to say, the interior of the sample chamber 46 is evacuated by an evacuation system 49 to a high degree of vacuum. The fluorescence X-rays 5 emitted from the surface of the sample 2 upon irradiation of the electron beam 1 thereto are detected by the detector 8. The detector 8, capable of energy analysis, is located between the electron lens systems 48 and 49 and is coaxially close to the electron beam 1. A detection signal from the detector 8 is processed by a controller 50 before being sent to a controller-processor 53 whereby the results of the analysis are displayed.

With the eleventh embodiment, a controller 51 controls the operating conditions of the electron source 44 and electron lens system 48 so that the acceleration energy of the electron beam 1 will be varied as needed between 0.1 keV and 200 keV. At low levels of acceleration energy, the eleventh embodiment analyzes residues qualitatively and quantitatively by detecting fluorescence X-rays from the sample surface as described above; at high levels of acceleration energy (>50 keV), the eleventh embodiment displays a scanning image of the surface of the sample 2 by detecting secondary and reflected electrons emanating from the sample surface. Because the electrons of highly accelerated energy are more likely to penetrate substances, detecting the reflected electrons makes it possible illustratively to observe the inner shape of small holes on the sample surface. An electron detector 54 is used to detect the secondary and reflected electrons emitted from the sample surface. This arrangement permits identification of the types of the elements making up the shape of the sample surface in addition to the observation of the latter.

The apparatus sketched schematically in FIG. 15 includes the function for measuring the lengths of fine patterns. The measurement of the lengths of fine patterns is accomplished by use of two additional means: means for measuring the location of the spot on the sample surface to which the electron beam is irradiated, and means for obtaining the distance between two different beam-irradiated spot locations on the basis of the data about the location of the spot on the sample surface thus measured by the means for measuring. A typical setup may involve using the controller 51 to control the electron lens systems 48 and 49 so that, with the surface of the sample 2 scanned by the electron beam 1, the controller-processor 53 displays on its display screen a secondary electron image of the sample surface. In that case, the acceleration energy of the electron beam 1 may be 5 keV or less. Observing the secondary electron image makes it possible to designate two points on the fine pattern to be measured for length. The distance between the two points (i.e., pattern length) is known by obtaining the amount of deflection of the electron beam 1 therebetween, or by acquiring the amount of movement of a stage 55 driven by a controller 52 therebetween.

As described and besides analyzing residues on the sample surface qualitatively and quantitatively, the eleventh embodiment is capable of observing the shape of the target residue on the sample surface and of measuring the sizes of small holes thereon. Thus the eleventh embodiment provides more generalized information about fine patterns on the sample surface than is conventionally offered.

Figure 16:
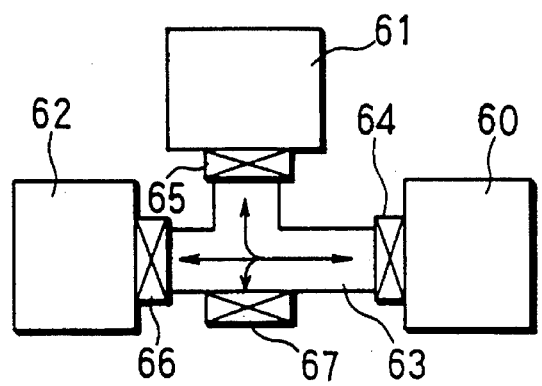
FIG. 16 is a schematic view of another surface analysis apparatus embodying the invention.

Twelfth Embodiment:

FIG. 16 schematically depicts a twelfth embodiment of the invention. This embodiment is an example in which the surface analysis apparatus of the invention is connected illustratively to equipment for fabricating semiconductors.

Referring to FIG. 16, a surface analysis apparatus 60 of the invention is connected to a path 63 via a gate valve 64. The inside of the path 63 is either evacuated or kept to a controlled atmosphere such as a nitrogen gas atmosphere. The path 63 has two other ends to which micro-fabrication apparatuses 61 and 62 are connected via gate valves 65 and 66, respectively. In the twelfth embodiment, the micro-fabrication apparatus 61 is implemented as an apparatus to form photo-resist patterns and the apparatus 62 as an etching apparatus.

Figure 17A:
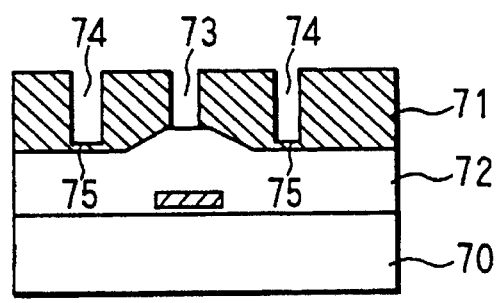
FIGS. 17 (A), 17 (B) and 17 (C) are schematic cross-sectional views showing some processes of fabricating semiconductor devices by use of another embodiment of the invention.
Figure 17B:
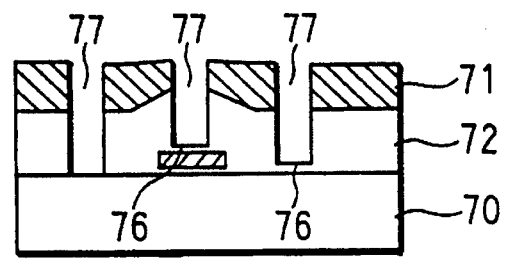
Figure 17C:
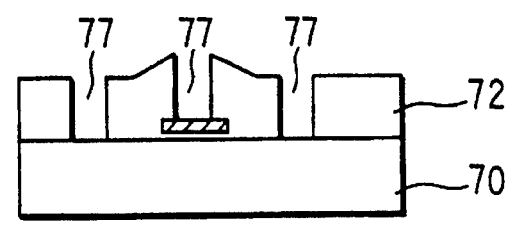

A typical process for semiconductor fabrication by use of the twelfth embodiment will now be described with reference to FIGS. 17 (A) through 17 (C). This process involves forming contact holes 77 on a non-conductive film 72 over a wafer (silicon substrate) 70.

First, the non-conductive film 72 on which to form contact holes is deposited over the wafer 70. A photo-sensitive resist layer 71 is coated over the non-conductive film 72. The wafer 70 is then introduced into the resist pattern forming apparatus 61 for resist pattern formation (FIG. 17 (A)). The formation of the resist pattern may be accomplished by use of known exposure and development apparatuses. The known exposure apparatuses include an ultraviolet exposure apparatus and an electron lithography apparatus, while the known development apparatuses comprise a wet development apparatus and a dry development apparatus using oxygen plasma.

After being subjected to pattern formation in the resist pattern forming apparatus 61, the wafer 70 moves on past the path 63 and enters the surface analysis apparatus 60 of the invention for examination. The surface analysis apparatus 60 distinguishes good holes 73 from defectively formed holes 74 with residual films left therein. Although FIGS. 17 (A) through 17 (C) are schematic cross-sectional views, it is impossible in practice to cut an in-process wafer for conventional cross-sectional observation. In particular, any residue in a deep hole can only be detected by use of the surface analysis apparatus 60 of the invention.

If the wafer 70 is judged to have defectively formed holes 74, the wafer 70 is placed back into the resist pattern forming apparatus 61 for additional development in accordance with the amount of the residue detected. Because the wafer 70 is transported through a vacuum or through a nitrogen gas atmosphere, there is no possibility of the pattern surface getting adversely affected. This improves the controllability of the additional development process. If the wafer were transported through the atmosphere, the oxidation of the resist pattern surface and the absorption of moisture thereinto could disable the additional development process.

With the satisfactory resist pattern thus formed, the wafer 70 is placed in the etching apparatus 62 for dry etching of the non-conductive film 72. If the non-conductive film 72 is a silicon oxide film, the wafer 70 is subjected to dry etching using Freon gas. Generally, the speed of dry etching on fine, deep holes is known to drop frequently, resulting in defectively formed contact holes.

After etching, the wafer 70 is moved again into the surface analysis apparatus 60 of the invention for surface analysis and examination. If the wafer 70 is found to have any etching residue 76 left inside an etched hole 77 as shown in FIG. 17 (B), the wafer 70 is judged to be etched defectively. The defectively etched wafer 70 is placed back into the etching apparatus 62 for additional etching. Eventually, good holes (contact holes) 77 completely free of etching residues are formed on the wafer 70 as depicted in FIG. 17 (C).

When small holes are formed on the wafer while the treated state thereof is being monitored by the surface analysis apparatus 60 of the invention, it is possible to achieve high yield in fabricating semiconductor devices free of poorly formed holes (e.g., contact holes). In the setup of FIG. 16, the surface analysis apparatus 60 of the invention need not be always connected to the micro-fabrication apparatuses 61 and 62; the component apparatuses may be connected only when needed via the gate valves 65 and 66. Needless to say, any other micro-fabrication apparatus may be connected as desired to the surface analysis apparatus 60 of the invention via a reserved gate valve 67 provided on the path 63.

Figure 18:
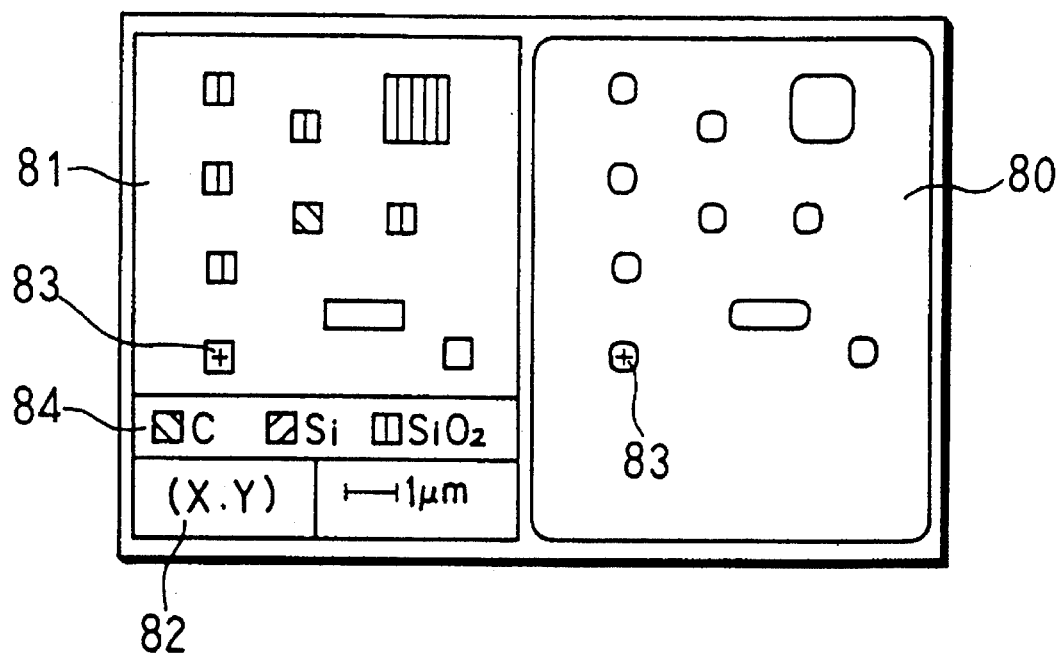
FIG. 18 is a schematic view of a display screen practiced by another embodiment of the invention.

Thirteenth Embodiment:

FIG. 18 is a schematic view of a thirteenth embodiment of the invention. When numerous small holes on the wafer are to be checked by the surface analysis apparatus of the invention with reference to semiconductor device patterns, the results of the analysis may be displayed effectively as follows:

The thirteenth embodiment involves displaying a real image 80 (secondary electron image) of the wafer surface pattern and a mask pattern image 81 side by side on a single screen. When coordinates of an analysis point 83 in the mask pattern image 81 are designated by use of an analysis point determination area 82, the wafer stage is controlled accordingly so that the real image 80 of the corresponding region including the analysis point 83 on the wafer surface is displayed immediately on the screen. It should be noted that the positioning of the wafer stage is generally not perfectly accurate; the wafer position is slightly dislodged from the designated location. This requires correcting the wafer position based on the image processing of the real image 80 in order to display a real image (secondary electron image) 80 that coincides with the mask pattern image 81. In this manner, analysis points (e.g., positions of the holes to be analyzed) are designated successively in the mask pattern image 81 for automated consecutive analysis. The results of the analysis are illustratively classified by color and displayed on a screen identifying the principal elements that were detected. A classifying and displaying area 84 showing a breakdown of the classified display may be included in the same display screen. Pointers 83 may be furnished in the mask pattern image 81 or real image (secondary electron image) 80 to indicate analysis points. These pointers help to verify successively whether or not the analysis points are correct.

Figure 19:
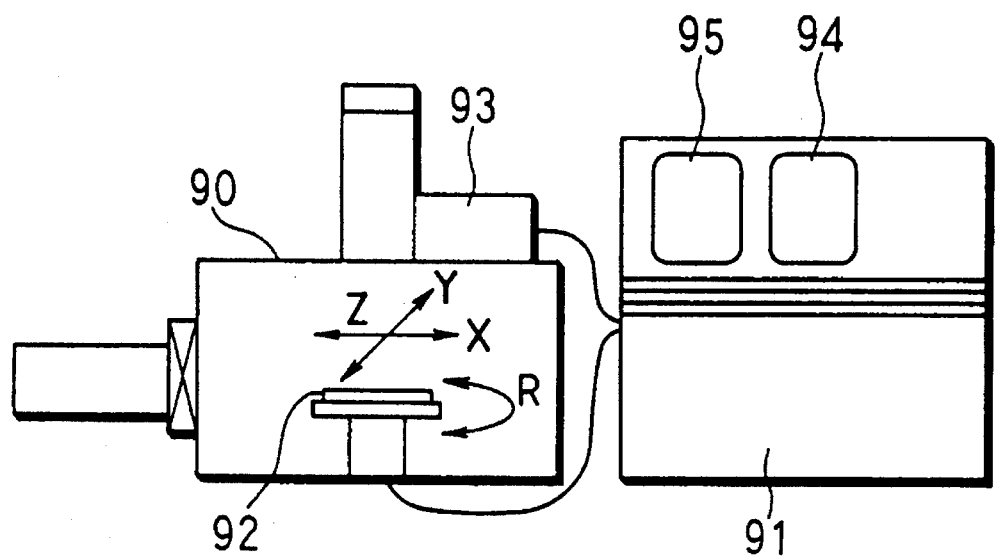
FIG. 19 is a schematic view of another surface analysis apparatus embodying the invention.

FIG. 19 is a schematic view of another surface analysis apparatus embodying the invention and comprising a mask information display screen 95. The apparatus includes an analysis part 90 and a control and display area 91. The control and display area 91 is made of a real image display screen 94 and another display screen 95 adjacent thereto. The real image display screen 94 displays a real image (secondary electron image) of the surface of a sample 92 (wafer) in accordance with a detection signal from a secondary electron detector 93. The display screen 95 displays mask information. Since semiconductor devices have a very large number of device patterns, the most efficient way to analyze the wafer surface is to display successively the design patterns (i.e., mask patterns) corresponding to the position of the wafer 92 and to designate desired analysis points consecutively in these mask patterns for analysis. The control and display area 91 may be arranged to admit process information on different wafer types. When a cross-sectional view of each designated position in a mask pattern is displayed on the mask information display screen 95, the results of the analysis are examined more efficiently.

As described above in conjunction with a number of embodiments, the invention utilizes various optical devices and X-ray detectors to observe the fluorescence X-rays emitted from the sample surface. To detect the fluorescence X-rays more effectively requires furnishing adjusting means for fine-adjusting the positions of the optical devices and detectors. These adjusting means may be additionally equipped with mechanisms, not shown, for fine adjustment of their positions. Needless to say, any combination of the above-described embodiments is also included in the scope of the invention. Furthermore, although not stated explicitly, the majority of the means for generating and detecting fluorescence X-rays are obviously set up in a vacuum. If the level of fluorescence X-rays absorbed by the particles in the atmosphere is sufficiently low, the sample may be placed in a vacuum of a relatively low degree.

As described in detail and according to the invention, a focused electron beam is irradiated to the sample surface and the fluorescence X-rays emitted from the residues thereon are observed near the axis of the electron beam. The scheme makes it possible to analyze qualitatively and quantitatively the residues with high accuracy even on an appreciably undulating surface of the sample. Since the surface analysis by the invention is non-destructive in nature, the analyzed sample can be placed unscathed back into the fabrication process.

As many apparently different embodiments of this invention may be made without departing from the spirit and scope thereof, it is to be understood that the invention is not limited to the specific embodiments thereof except as defined in the appended claims.

We claim:

1. A surface analysis method for analyzing residues inside small holes on the surface of a sample by irradiating an accelerated and focused electron beam into said small holes and by observing fluorescence X-rays emitted therefrom in return, said surface analysis method comprising the step of observing said fluorescence X-rays within an angle $\alpha$ with respect to the center axis of the electron beam, said angle being defined as $$\tan \alpha = (a/d)$$

where, a multiplied by 2 stands for the inner diameter of any one of said small holes and d for the depth thereof.

2. A surface analysis method according to claim 1, wherein said residues include at least one atom selected from the group consisting of carbon atoms, oxygen atoms and silicon atoms.

3. A surface analysis method according to claim 1, wherein the energy of said electron beam is such as to excite, for the purpose of fluorescence X-ray emission from said sample, at least one atom selected from the group consisting of carbon atoms, oxygen atoms and silicon atoms.

4. A surface analysis method according to claim 1, wherein the energy of said electron beam is not greater than 5 keV.

5. A surface analysis method according to claim 1, wherein the energy of said electron beam is not greater than 10 times the energy of the fluorescence X-rays to be observed.

6. A surface analysis method according to claim 1, wherein said fluorescence X-rays are observed by use of an annular X-ray detector which spectrally detects said fluorescence X-rays, said annular X-ray detector having a center hole coaxially arranged around the center axis of said electron beam.

7. A surface analysis method according to claim 6, wherein said electron beam is irradiated onto the sample surface through said center hole of said X-ray detector.

8. A surface analysis method according to claim 1, wherein said fluorescence X-rays are observed by use of an X-ray detector located on or near the center axis of said electron beam, said X-ray detector detecting said fluorescence X-rays spectrally.

9. A surface analysis method according to claim 8, wherein said electron beam is deflected to bypass said X-ray detector before being irradiated onto the sample surface.

10. A surface analysis method according to claim 7, wherein said X-ray detector is located inside an electron lens for focusing said electron beam.

11. A surface analysis method according to claim 1, wherein said fluorescence X-rays are observed by use of an X-ray reflector located near the center axis of said electron beam and by use of an X-ray detector located outside said center axis of said electron beam, said X-ray reflector reflecting said fluorescence X-rays, the reflected X-rays being spectrally detected by said X-ray detector.

12. A surface analysis method according to claim 11, wherein said X-ray reflector is a total reflector for totally reflecting said fluorescence X-rays.

13. A surface analysis method according to claim 11, wherein said X-ray reflector is a plane mirror.

14. A surface analysis method according to claim 11, wherein said X-ray reflector is a mirror selected from the group consisting of cylindrical mirrors, spherical mirrors, toroidal mirrors, and non-spherical mirrors comprising a revolutional conicoid each.

15. A surface analysis method according to claim 11, wherein the curvature of the reflecting surface of said X-ray reflector is variable.

16. A surface analysis method according to claim 1, wherein said fluorescence X-rays are observed by use of a multilayer film reflector located near the center axis of said electron beam and by use of an X-ray detector located outside said center axis of said electron beam, said multilayer film reflector spectrally reflecting said fluorescence X-rays, the spectrally reflected fluorescence X-rays being detected by said X-ray detector.

17. A surface analysis method according to claim 16, wherein said multilayer film reflector is rotated to vary the spectral condition of said fluorescence X-rays, said X-ray detector being relocated in synchronism with the rotation of said multilayer film reflector so as to detect said spectrally reflected fluorescence X-rays.

18. A surface analysis method according to claim 16, wherein said X-ray detector is a two-dimensional detector having a plurality of X-ray detecting devices arranged two-dimensionally.

19. A surface analysis method according to claim 1, wherein said fluorescence X-rays are observed by use of diffraction gratings located near the center axis of said electron beam and by use of an X-ray detector located outside said center axis of said electron beam, said diffraction gratings spectrally reflecting said fluorescence X-rays, the spectrally reflected fluorescence X-rays being detected by said X-ray detector.

20. A surface analysis method according to claim 19, wherein said X-ray detector is a two-dimensional detector having a plurality of X-ray detecting devices arranged two-dimensionally.

21. A surface analysis method according to claim 1, wherein said electron beam is deflected immediately before incidence on the sample surface.

22. A surface analysis method according to claim 1, wherein that spot on the sample surface to which said electron beam is irradiated is heated locally.

23. A surface analysis method according to claim 22, wherein the local heating is carried out at a temperature between 100° C. and 200° C.

24. A surface analysis method according to claim 23, wherein the local heating is carried out by focusing a light beam onto the spot to be heated.

25. A surface analysis method according to claim 22, wherein the local heating is carried out by focusing a light beam onto the spot to be heated.

26. A surface analysis method according to claim 25, wherein said light beam is either a visible ray beam or an infrared ray beam.

27. A surface analysis method for analyzing residues on the surface of a sample by irradiating an accelerated and focused electron beam onto the sample surface and by observing fluorescence X-rays emitted therefrom in return, said surface analysis method comprising the step of observing said fluorescence X-rays within an angle of 20 degrees with respect to the center axis of the electron beam.

28. A surface analysis method according to claim 27, wherein said residues include at least one atom selected from the group consisting of carbon atoms, oxygen atoms and silicon atoms.

29. A surface analysis method according to claim 27, wherein the energy of said electron beam is such as to excite, for the purpose of fluorescence X-ray emission from said sample, at least one atom selected from the group consisting of carbon atoms, oxygen atoms and silicon atoms.

30. A surface analysis method according to claim 27, wherein the energy of said electron beam is not greater than 5 keV.

31. A surface analysis method according to claim 27, wherein the energy of said electron beam is not greater than 10 times the energy of the fluorescence X-rays to be observed.

32. A surface analysis method according to claim 27, wherein said fluorescence X-rays are observed by use of an annular X-ray detector which spectrally detects said fluorescence X-rays, said annular X-ray detector having a center hole coaxially arranged around the center axis of said electron beam.

33. A surface analysis method according to claim 27, wherein said fluorescence X-rays are observed by use of an X-ray detector located on or near the center axis of said electron beam, said X-ray detector detecting said fluorescence X-rays spectrally.

34. A surface analysis method according to claim 27, wherein said fluorescence X-rays are observed by use of an X-ray reflector located near the center axis of said electron beam and by use of an X-ray detector located outside said center axis of said electron beam, said X-ray reflector reflecting said fluorescence X-rays, the reflected X-rays being spectrally detected by said X-ray detector.

35. A surface analysis method according to claim 27, wherein said fluorescence X-rays are observed by use of a multilayer film reflector located near the center axis of said electron beam and by use of an X-ray detector located outside said center axis of said electron beam, said multilayer film reflector spectrally reflecting said fluorescence X-rays, the spectrally reflected fluorescence X-rays being detected by said X-ray detector.

36. A surface analysis method according to claim 27, wherein said fluorescence X-rays are observed by use of diffraction gratings located near the center axis of said electron beam and by use of an X-ray detector located outside said center axis of said electron beam, said diffraction gratings spectrally reflecting said fluorescence X-rays, the spectrally reflected fluorescence X-rays being detected by said X-ray detector.

37. A surface analysis method according to claim 27, wherein said electron beam is deflected immediately before incidence on the sample surface.

38. A surface analysis method according to claim 27, wherein that spot on the sample surface to which said electron beam is irradiated is heated locally.

39. A surface analysis apparatus comprising electron beam irradiating means for irradiating a finely focused electron beam into small holes on the surface of a sample, and fluorescence X-ray observing means for observing fluorescence X-rays emitted from said small holes in response to the irradiation of the electron beam, wherein said fluorescence X-ray observing means includes a function for spectrally detecting said fluorescence X-rays emitted within an angle $\alpha$ with respect to the center axis of said electron beam, said angle being defined as $$\tan \alpha = (a/d)$$

where, a multiplied by 2 stands for the inner diameter of any one of said small holes and d for the depth thereof.

40. A surface analysis apparatus according to claim 39, wherein the energy of said electron beam is such as to excite, for the purpose of fluorescence X-ray emission from said sample, at least one atom selected from the group consisting of carbon atoms, oxygen atoms and silicon atoms on the sample surface.

41. A surface analysis apparatus according to claim 39, wherein the energy of said electron beam is not greater than 5 keV.

42. A surface analysis apparatus according to claim 39, wherein the energy of said electron beam is not greater than 10 times the energy of the fluorescence X-rays to be observed.

43. A surface analysis apparatus according to claim 39, wherein said fluorescence X-ray observing means includes an annular X-ray detector capable of analyzing energy, said annular X-ray detector having a center hole coaxially arranged around the center axis of said electron beam, and wherein said electron beam irradiating means is arranged to irradiate said electron beam onto the sample surface through the center hole of the X-ray detector.

44. A surface analysis apparatus according to claim 39, wherein said fluorescence X-ray observing means includes an X-ray detector capable of analyzing energy and located on the center axis of said electron beam, and wherein said electron beam irradiating means is arranged to deflect said electron beam to bypass said X-ray detector before irradiating said electron beam onto the sample surface.

45. A surface analysis apparatus according to claim 43, wherein said electron beam irradiating means includes an electron lens for focusing said electron beam, said annular X-ray detector being located inside said electron lens.

46. A surface analysis apparatus according to claim 39, wherein said fluorescence X-ray observing means includes an X-ray reflector located near the center axis of said electron beam irradiated onto the sample surface, and an X-ray detector capable of analyzing energy, said X-ray detector detecting said fluorescence X-rays reflected by said X-ray reflector.

47. A surface analysis apparatus according to claim 46, wherein said X-ray reflector is a total reflector for totally reflecting said fluorescence X-rays.

48. A surface analysis apparatus according to claim 46, wherein said X-ray reflector is a plane mirror.

49. A surface analysis apparatus according to claim 46, wherein said X-ray reflector is a mirror selected from the group consisting of cylindrical mirrors, spherical mirrors, toroidal mirrors, and non-spherical mirrors comprising a revolutional conicoid each.

50. A surface analysis apparatus according to claim 46, wherein said fluorescence X-ray observing means includes means for varying the curvature of the reflecting surface of said X-ray reflector.

51. A surface analysis apparatus according to claim 39, wherein said fluorescence X-ray observing means includes a multilayer film X-ray reflector located near the center axis of said electron beam irradiated onto the sample surface, and an X-ray detector for detecting the fluorescence X-rays reflected spectrally by said multilayer film X-ray reflector.

52. A surface analysis apparatus according to claim 51, wherein said fluorescence X-ray observing means includes rotating means for rotating said multilayer film X-ray reflector to vary the incidence angle of the fluorescence X-rays that are incident on said multilayer film X-ray reflector, and moving means for moving said X-ray detector in cooperation with the rotation of said multilayer film X-ray reflector so that said X-ray detector may detect the fluorescence X-rays reflected spectrally by said multilayer film X-ray reflector.

53. A surface analysis apparatus according to claim 39, wherein said fluorescence X-ray observing means includes diffraction gratings located near the center axis of said electron beam irradiated onto the sample surface, and an X-ray detector for detecting the fluorescence X-rays reflected spectrally by said diffraction gratings.

54. A surface analysis apparatus according to claim 53, wherein said X-ray detector is a two-dimensional detector having a plurality of X-ray detecting devices arranged two-dimensionally.

55. A surface analysis apparatus according to claim 51, wherein said X-ray detector is a two-dimensional detector having a plurality of X-ray detecting devices arranged two-dimensionally.

56. A surface analysis apparatus according to claim 39, wherein said electron beam irradiating means includes deflecting means for deflecting said electron beam immediately before incidence on the sample surface.

57. A surface analysis apparatus according to claim 39, further comprising heating means for locally heating that spot on the sample surface to which said electron beam is irradiated.

58. A surface analysis apparatus according to claim 57, wherein said heating means carries out the local heating at a temperature between 100° C. and 200° C. on that spot of the sample surface to which said electron beam is irradiated.

59. A surface analysis apparatus according to claim 57, wherein said heating means includes light beam irradiating means for irradiating a focused light beam onto that spot of the sample surface to which said electron beam is irradiated.

60. A surface analysis apparatus according to claim 59, wherein said light beam irradiating means includes a light source and a condenser lens for focusing light from said light source onto the spot to be heated on said sample surface.

61. A surface analysis apparatus according to claim 59, wherein said light is either visible rays or infrared rays.

62. A surface analysis apparatus according to claim 39, further comprising measuring means for measuring a location of a spot on the sample surface to which said electron beam is irradiated, and calculating means for calculating the distance between two different beam irradiated spot locations with reference to the location of the spot on the sample surface measured by said measuring means.

63. A composite apparatus for fabricating semiconductors comprising the surface analysis apparatus of claim 39, a fabrication apparatus for finely fabricating the surface of a sample, and a transport apparatus for transporting said sample between said surface analysis apparatus and said fabrication apparatus.

64. A surface analysis apparatus according to claim 39, further comprising means for automatically determining the location to be analyzed on the sample surface in accordance with the data of the pattern coordinates established on the sample surface.

65. A surface analysis apparatus according to claim 64, further comprising display means for displaying both the pattern coordinate data and an observed picture of a sample surface area including said location to be analyzed.

66. A surface analysis apparatus according to claim 65, wherein said display means has a function for displaying a schematic cross-sectional view of the sample surface area designated by the process data resulting from the surface processing carried out on the sample surface to be analyzed.

67. A surface analysis apparatus comprising electron beam irradiating means for irradiating a finely focused electron beam onto the surface of a sample, and fluorescence X-ray observing means for observing fluorescence X-rays emitted from the sample surface in response to the irradiation of the electron beam, wherein said fluorescence X-ray observing means includes a function for spectrally detecting said fluorescence X-rays emitted within an angle of 20 degrees with respect to the center axis of said electron beam.

68. A surface analysis apparatus according to claim 67, wherein the energy of said electron beam is such as to excite, for the purpose of fluorescence X-ray emission from said sample, at least one atom selected from the group consisting of carbon atoms, oxygen atoms and silicon atoms on the sample surface.

69. A surface analysis apparatus according to claim 67, wherein the energy of said electron beam is not greater than 5 keV.

70. A surface analysis apparatus according to claim 67, wherein the energy of said electron beam is not greater than 10 times the energy of the fluorescence X-rays to be observed.

71. A surface analysis apparatus according to claim 67, wherein said fluorescence X-ray observing means includes an annular X-ray detector capable of analyzing energy, said annular X-ray detector having a center hole coaxially arranged around the center axis of said electron beam, and wherein said electron beam irradiating means is arranged to irradiate said electron beam onto the sample surface through the center hole of the X-ray detector.

72. A surface analysis apparatus according to claim 67, wherein said fluorescence X-ray observing means includes an X-ray detector capable of analyzing energy and located on the center axis of said electron beam, and wherein said electron beam irradiating means is arranged to deflect said electron beam to bypass said X-ray detector before irradiating said electron beam onto the sample surface.

73. A surface analysis apparatus according to claim 67, wherein said fluorescence X-ray observing means includes an X-ray reflector located near the center axis of said electron beam irradiated onto the sample surface, and an X-ray detector capable of analyzing energy, said X-ray detector detecting said fluorescence X-rays reflected by said X-ray reflector.

74. A surface analysis apparatus according to claim 67, wherein said fluorescence X-ray observing means includes a multilayer film X-ray reflector located near the center axis of said electron beam irradiated onto the sample surface, and an X-ray detector for detecting the fluorescence X-rays reflected spectrally by said multilayer film X-ray reflector.

75. A surface analysis apparatus according to claim 67, wherein said fluorescence X-ray observing means includes diffraction gratings located near the center axis of said electron beam irradiated onto the sample surface, and an X-ray detector for detecting the fluorescence X-rays reflected spectrally by said diffraction gratings.

76. A surface analysis apparatus according to claim 67, wherein said electron beam irradiating means includes deflecting means for deflecting said electron beam immediately before incidence on the sample surface.

77. A surface analysis apparatus according to claim 67, further comprising heating means for locally heating that spot on the sample surface to which said electron beam is irradiated.

78. A surface analysis apparatus according to claim 67, further comprising measuring means for measuring a location of a spot on the sample surface to which said electron beam is irradiated, and calculating means for calculating the distance between two different beam irradiated spot locations with reference to the location of the spot on the sample surface measured by said measuring means.

79. A composite apparatus for fabricating semiconductors comprising the surface analysis apparatus of claim 67, a fabrication apparatus for finely fabricating the surface of a sample, and a transport apparatus for transporting said sample between said surface analysis apparatus and said fabrication apparatus.

80. A surface analysis apparatus according to claim 67, further comprising means for automatically determining the location to be analyzed on the sample surface in accordance with data of pattern coordinates established on the sample surface.

* * * * *